(12) United States Patent
Komeda et al.

(10) Patent No.: US 6,732,738 B1
(45) Date of Patent: May 11, 2004

(54) METHOD TO ENHANCE HEALING OF STERNUM AFTER STERNOTOMY

(75) Inventors: Masashi Komeda, Urbanlife 303, 256, Daimon-cho Sawaragi-cho Kudaru Muromachidori Kamigyo-ku, Kyoto-shi Kyoto-fu (JP); Yasuhiko Tabata, 8-16, Biwadai 3-chome, Uji-shi Kyoto-fu (JP)

(73) Assignees: Masashi Komeda, Kyoto-fu (JP); Yasuhiko Tabata, Kyoto-fu (JP); Kaken Pharmaceutical Company, Ltd., Tokyo (JP)

( * ) Notice: Subject to any disclaimer, the term of this patent is extended or adjusted under 35 U.S.C. 154(b) by 213 days.

(21) Appl. No.: 09/687,379

(22) Filed: Oct. 13, 2000

Related U.S. Application Data

(63) Continuation-in-part of application No. 09/408,804, filed on Sep. 30, 1999.

(51) Int. Cl.⁷ .............................. A61B 19/00; A61F 2/00
(52) U.S. Cl. ......................................... 128/898; 424/423
(58) Field of Search ...................... 128/898; 424/198.1, 424/423, 422, 426; 514/43, 12; 530/355; 623/23.51, 23.54, 23.59, 23.6, 23.75, 23.76

(56) References Cited

U.S. PATENT DOCUMENTS

| | | | | |
|---|---|---|---|---|
| 5,270,300 A | * | 12/1993 | Hunziker | 514/12 |
| 6,123,731 A | * | 9/2000 | Boyce et al. | 623/23.63 |
| 6,294,041 B1 | * | 9/2001 | Boyce et al. | 156/275.5 |
| 6,294,187 B1 | * | 9/2001 | Boyce et al. | 424/422 |
| 6,440,444 B2 | * | 8/2002 | Boyce et al. | 424/422 |
| 6,454,794 B1 | * | 9/2002 | Knudson et al. | 623/1.1 |
| 6,478,825 B1 | * | 11/2002 | Winterbottom et al. | 623/23.63 |

FOREIGN PATENT DOCUMENTS

| | | |
|---|---|---|
| EP | 493 737 A1 | 12/1991 |
| EP | 702 959 A1 | 5/1994 |

OTHER PUBLICATIONS

Yasuhiko Tabata et al., "Bone Regeneration by Basic Fibroblast Growth Factor Complexed with Biodegradable Hydrogels." *Biomaterials*, 19:807–816 (1998).

Keisuke Yamada et al., "Potential Efficacy of Basic Fibroblast Growth Factor Incorporated in Biodegradable Hydrogels for Skull Bone Regeneration." *J. Neurosurg.* 86:871–875 (1997).

* cited by examiner

*Primary Examiner*—David J. Isabella
(74) *Attorney, Agent, or Firm*—Nixon Peabody LLP

(57) ABSTRACT

There are disclosed a method to enhance sternal treatment after sternotomy with or without removal of at least one of thoracic arteries which comprises applying an agent for the treatment of sternum after sternotomy to or at around the sternum, wherein the agent comprises at least one selected from the group consisting of an angiogenetic factor, an osteogenetic factor and their analogues such as bFGF, aFGF, TGF β, VEGF, HGF, BMP, PDGF, TGF α, other cytokines or gene as an effective ingredient and an agent to be used for the method; and an agent to enhance healing of or treating sternum after sternotomy comprising the same.

14 Claims, 13 Drawing Sheets

Group A (bFGF)

Group A (bFGF)

Group B (Control)

Group C (Sham)

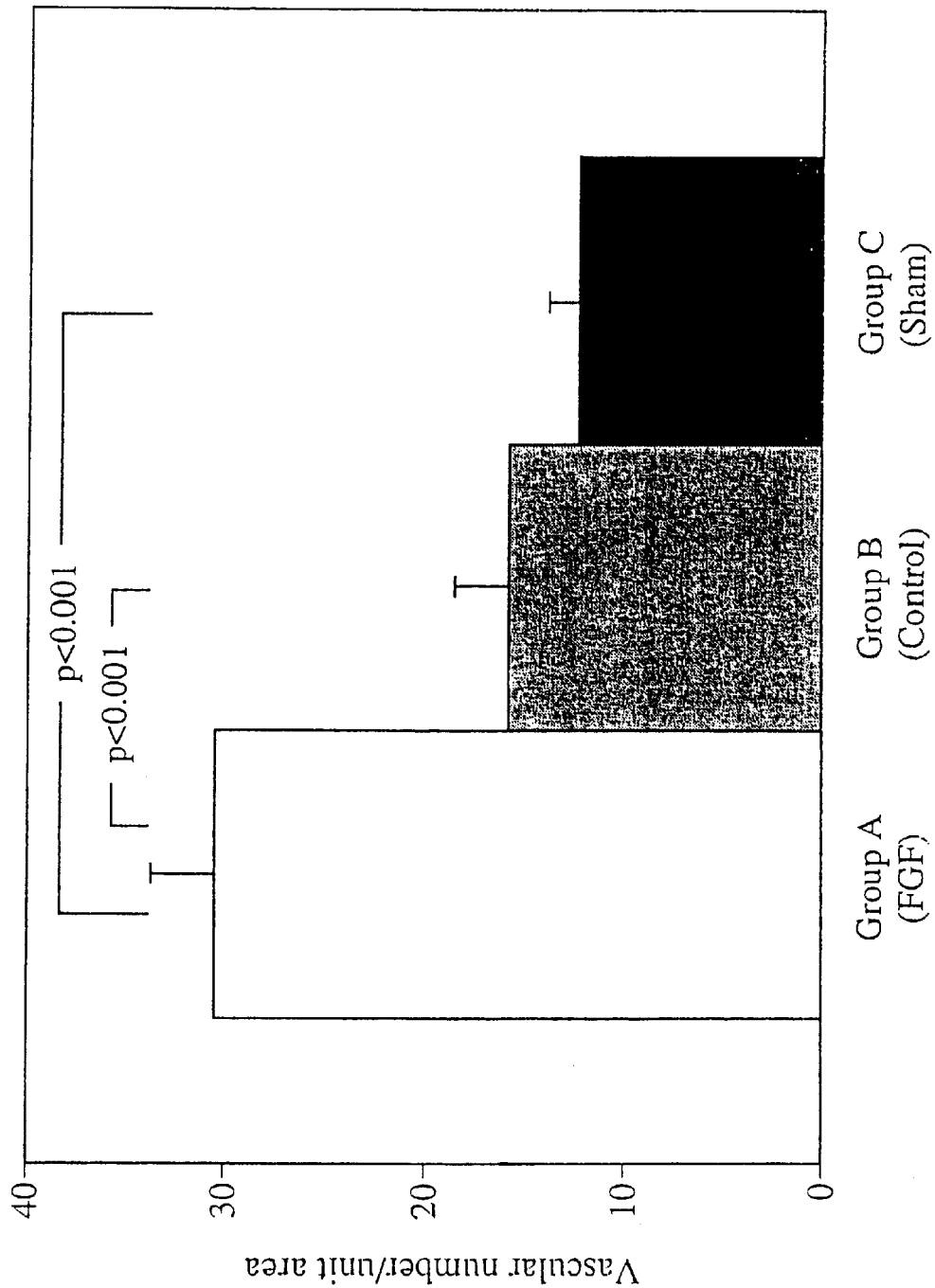

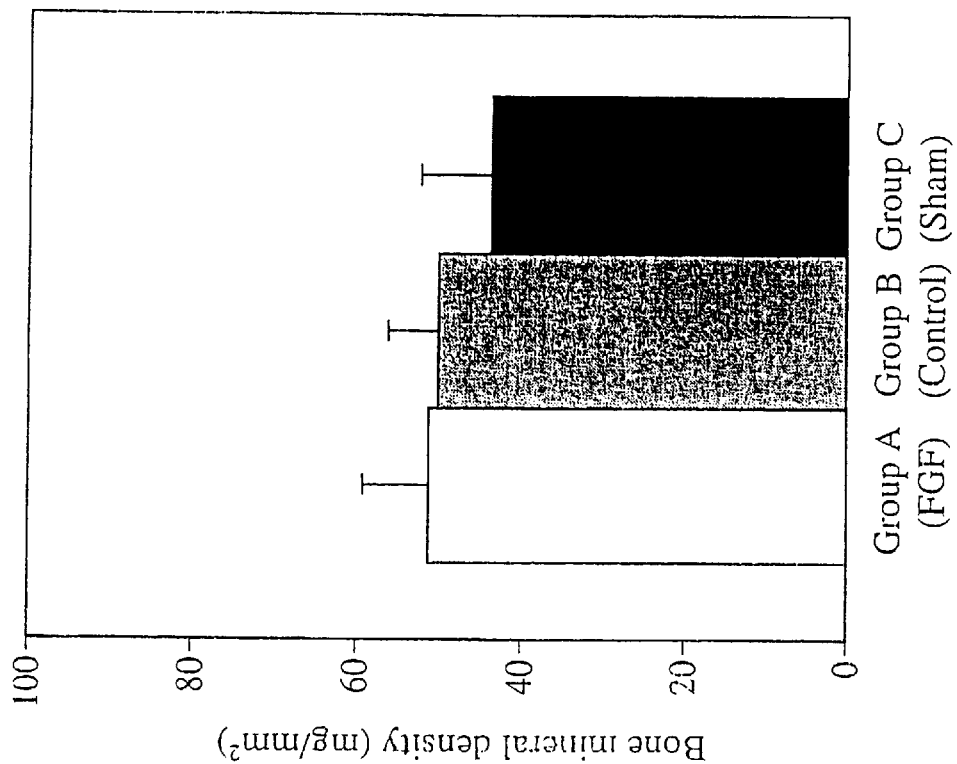
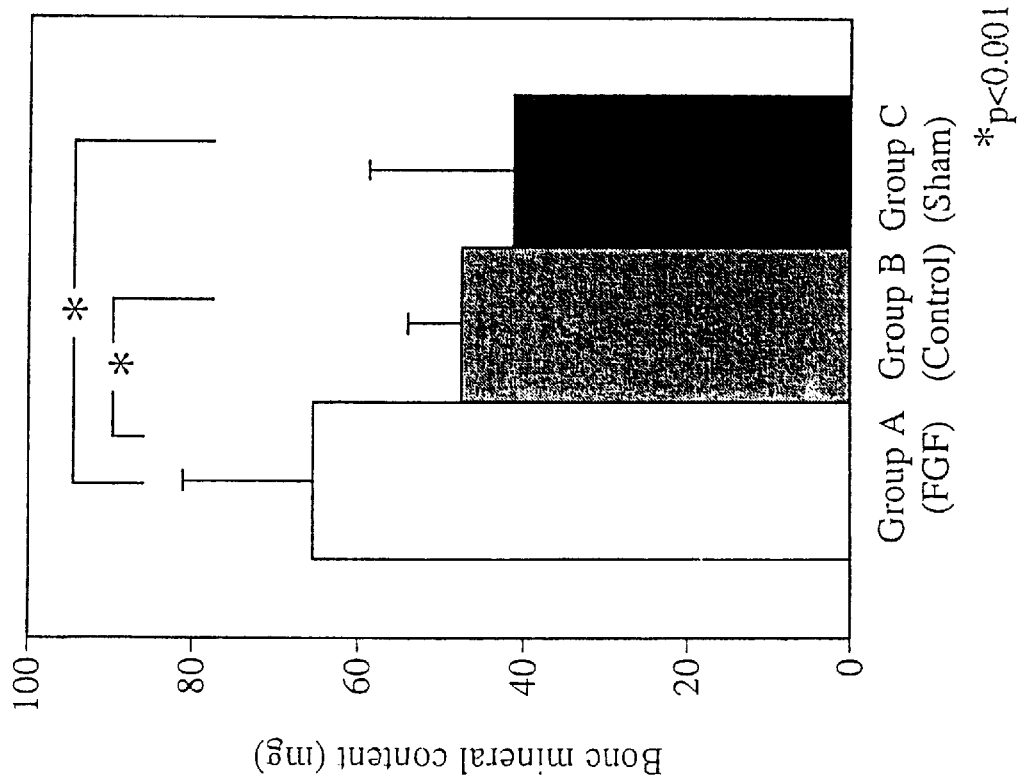
Fig. 4A
Fig. 4B

Group A (bFGF)

Group B (Control)

Group C (Sham)

Group A (bFGF)

Group B (Control)

Group C (Sham)

Group A (bFGF)

Group B (Control)

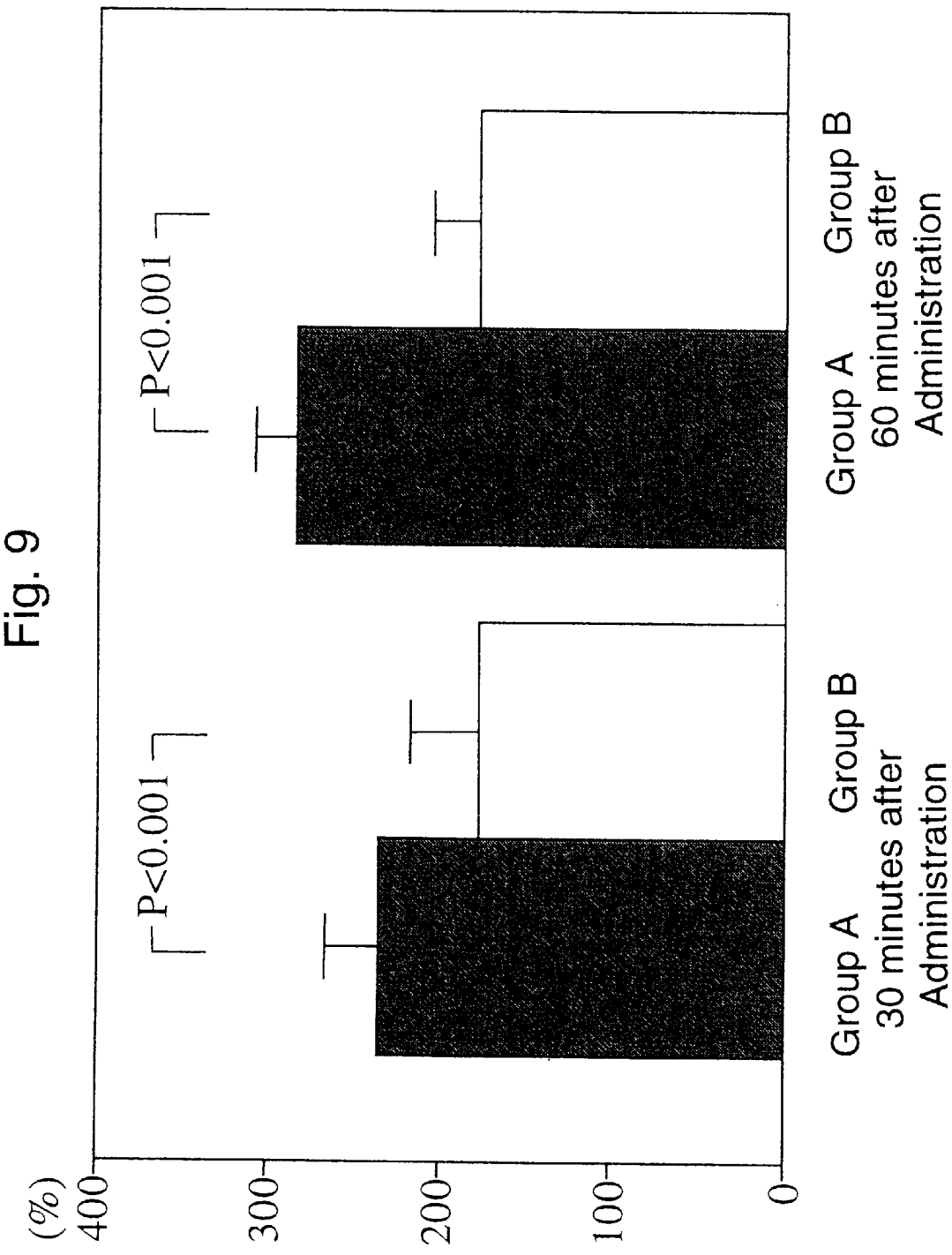

Group A (bFGF)

Group B (Control)

METHOD TO ENHANCE HEALING OF STERNUM AFTER STERNOTOMY

CROSS REFERENCE TO RELATED APPLICATIONS

This application is a continuation-in-part of U.S. application Ser. No. 09/408,804, filed on Sep. 29, 1999, now abandoned.

FIELD OF THE INVENTION

The present invention relates to a method to enhance healing of sternum after sternotomy (i.e., cutting sternum to approach heart) in operations such as open heart surgery or coronary artery surgery including the sternotomy with removal of at least one of internal thoracic arteries (hereinafter sometimes referred to as "ITA"), using an agent containing angiogenetic factor(s).

BACKGROUND ART

Sternotomy is almost always necessary to operate on heart with various heart disease such as coronary artery disease including myocardial infarction and its mechanical complications, valvular heart disease, aortic disease, and congenital heart disease. However, it takes time for sternum to heal and sometimes it does not heal well.

Slow or poor healing of the sternum is one of the problems after the sternotomy therefore heart surgery. Slow healing prolongs patients' hospital stay and increases health care cost considerably, and delays patients return to work or social activity. Poor healing of the sternum is one of the serious problems after heart operations performed though a sternotomy, and often causes deep sternal wound infection that results in increased mortality and morbidity in spite of expensive intensive care. Previous studies described the risk factors for poor sternal healing as follows: obesity, chronic obstructive pulmonary disease (such as chronic bronchitis or emphysema), elderly age, peripheral vascular disease, reoperation, diabetes mellitus, use of internal thoracic artery (ITA) conduit(s), operation time, low cardiac output, mechanical ventilation time, and reexploration for bleeding. Increasing number of patients have some of above risk factors and slow/poor sternal healing will be even more problematical. Slow/poor sternal healing often limits the use of bilateral internal thoracic arteries (hereinafter sometimes referred to as "BITA") in coronary bypass surgery especially in diabetic patients whose hearts are shown to benefit form BITA grafting, because diabetic patients often develop sternal necrosis (i.e., dead sternum bone) particularly after BITA removal (i.e., to make grafts for heart) due to lack of blood supply.

It has been reported that a basic fibroblast growth factor (hereinafter sometimes referred to as "bFGF") is not only an intense angiogenetic (i.e., create new vessels and increase blood supply to the sternum) mitogen but also can stimulate bone formation. Other growth factors such as aFGF, VEGF, TGF β have more or less benefit in enhancing the sternal healing via their angiogenetic effects.

Some of the present inventors have already proposed to use an agent containing bFGF for treating bone disease in EP-A-0 493 737 and a cross-linked gelatin gel preparation containing bFGF in EP-A-0 702 959. That is, some of the present inventors have already proposed to use an agent containing bFGF for the treatment of bone diseases in EP-A-0 493 737 and a cross-linked gelatin gel preparation containing bFGF in EP-A-0 702 959. In EP-A-0 493 737, a novel agent for the treatment of bone diseases such as various traumatic fractures, various fatigue fractures, pathologic fractures including fracture accompanied by osteoporosis, osteomalacia, malignant tumor, multiple myeloma, etc., reduction in bone strength accompanied by various diseases as mentioned above, and inhibition of bone formation accompanied by various diseases as mentioned above. In EP-A-0 702 959, there is disclosed a hemoglobin level increasing effect, a bone mineral content increasing effect, and the like. They have demonstrated that gelatin hydrogels which incorporated bFGF enhanced the in vivo angiogenetic effect and bone regeneration.

Moreover, some of the present inventors have reported in "J. Neurosurg., Vol. 86, pp. 871–875 (1997)" potential efficacy of bFGF incorporated in biodegradable hydrogels for skull bone regeneration using a rabbit model and in "Biomaterials, vol. 19, pp. 807–815 (1998)" bone regeneration by bFGF complexed with biodegradable hydrogels of skull bone defects which has been clinically recognized as almost impossible. However, in either of the above-mentioned references, there is no description about healing of sternum after sternotomy including the sternotomy with ITA removal. Sternum has a different shape and blood supply (i.e., different feeding arteries) from that of the skull bone or long bones; the difference is more obvious after sternotomy (i.e., almost always longitudinal cut rather than transverse cut).

SUMMARY OF THE INVENTION

An object of the present invention is to provide a method to enhance healing of the sternum after sternotomy including the sternotomy with the BITA removal, which can shorten patients' hospitalization and can decrease complications related to poor sternal healing, and therefore will reduce health care cost, will facilitate patients' return to work and will help increase their productivity. The present invention can effectively heal the sternum by using an agent containing angiogenetic or osteogenetic factor(s).

In an attempt to conquest the problem of slow or poor sternal healing after sternotomy, the present inventors have developed a few methods to enhance sternal healing as described below. In short, the present invention applies one or more of the above angiogenetic factors or their gene to the sternum or the tissue around to enhance angiogenesis in order to offset the shortness of blood supply for the sternum or to help osteogenesis (i.e., help create bone tissue for the sternum) to stabilized the sternum and help sternal healing.

That is, the present invention relates to a method to enhance healing of or treating sternum after sternotomy with or without removal of at least one of thoracic arteries which comprises applying an agent for the treatment of sternum after sternotomy to or at around the sternum, wherein said agent comprises at least one selected from the group consisting of an angiogenetic factor, an osteogenetic factor and their analogues as an effective ingredient.

The present invention also relates to a method of regenerating bone at sternum after sternotomy or sternotomy with or without removal of at least one of internal thoracic arteries which comprises applying an agent for the treatment of sternum after sternotomy to or at around the sternum, wherein said agent comprises at least one selected from the group consisting of an angiogenetic factor, an osteogenetic factor and their analogues as an effective ingredient.

The present invention further relates to a method of subjecting to vascularization around sternum after sternotomy or sternotomy with or without removal of at least one of internal thoracic arteries which comprises applying an agent for the treatment of sternum after sternotomy to or at around the sternum, wherein said agent comprises at least one selected from the group consisting of an angiogenetic factor, an osteogenetic factor and their analogues as an effective ingredient.

Moreover, the present invention relates to a method of treating a fracture site after sternotomy with or without removal of at least one of internal thoracic arteries which comprises applying an agent for the treatment of the fracture site after sternotomy in direct contact with the fracture site of a rib, cartilage or their junction, wherein said agent comprises at least one selected from the group consisting of an angiogenetic factor, an osteogenetic factor and their analogues as an effective ingredient.

Also, the present invention relates to an agent to enhance healing of or treating sternum after sternotomy with or without removal of at least one of thoracic arteries by applying the agent for the treatment of sternum after sternotomy to or at around the sternum, wherein said agent comprises at least one selected from the group consisting of an angiogenetic factor, an osteogenetic factor and their analogues as an effective ingredient.

The present invention also relates to an agent of regenerating bone at sternum after sternotomy or sternotomy with or without removal of at least one of internal thoracic arteries by applying the agent for the treatment of sternum after sternotomy to or at around the sternum, wherein said agent comprises at least one selected from the group consisting of an angiogenetic factor, an osteogenetic factor and their analogues as an effective ingredient.

The present invention further relates to an agent of subjecting to vascularization around sternum after sternotomy or sternotomy with or without removal of at least one of internal thoracic arteries by applying the agent for the treatment of sternum after sternotomy to or at around the sternum, wherein said agent comprises at least one selected from the group consisting of an angiogenetic factor, an osteogenetic factor and their analogues as an effective ingredient.

Moreover, the present invention relates to an agent of treating a fracture site after sternotomy with or without removal of at least one of internal thoracic arteries by applying an agent for the treatment of the fracture site after sternotomy in direct contact with the fracture site of a rib, cartilage or their junction, wherein said agent comprises at least one selected from the group consisting of an angiogenetic factor, an osteogenetic factor and their analogues as an effective ingredient.

BRIEF DESCRIPTION OF THE DRAWINGS

FIGS. 2A to 2C are photomicrographs of the connective tissue around the sternum four weeks after surgery, wherein FIG. 2A is Group A (bFGF), FIG. 2B is Group B (control) and FIG. 2C is Group C (sham);

FIG. 3 is a graph showing comparison of the vascular number around the sternum among three groups;

FIGS. 4A and 4B are graphs showing comparison of bone mineral content and bone mineral density among three groups, respectively, wherein Group A is bFGF, Group B is control and Group C is sham;

FIG. 9 is a graph showing comparison of bone scintigram after 30 minutes and 60 minutes from administration of $^{99m}$Tc-MPD among two groups four weeks after surgery;

DESCRIPTION OF THE PREFERRED EMBODIMENTS

Figure 1:
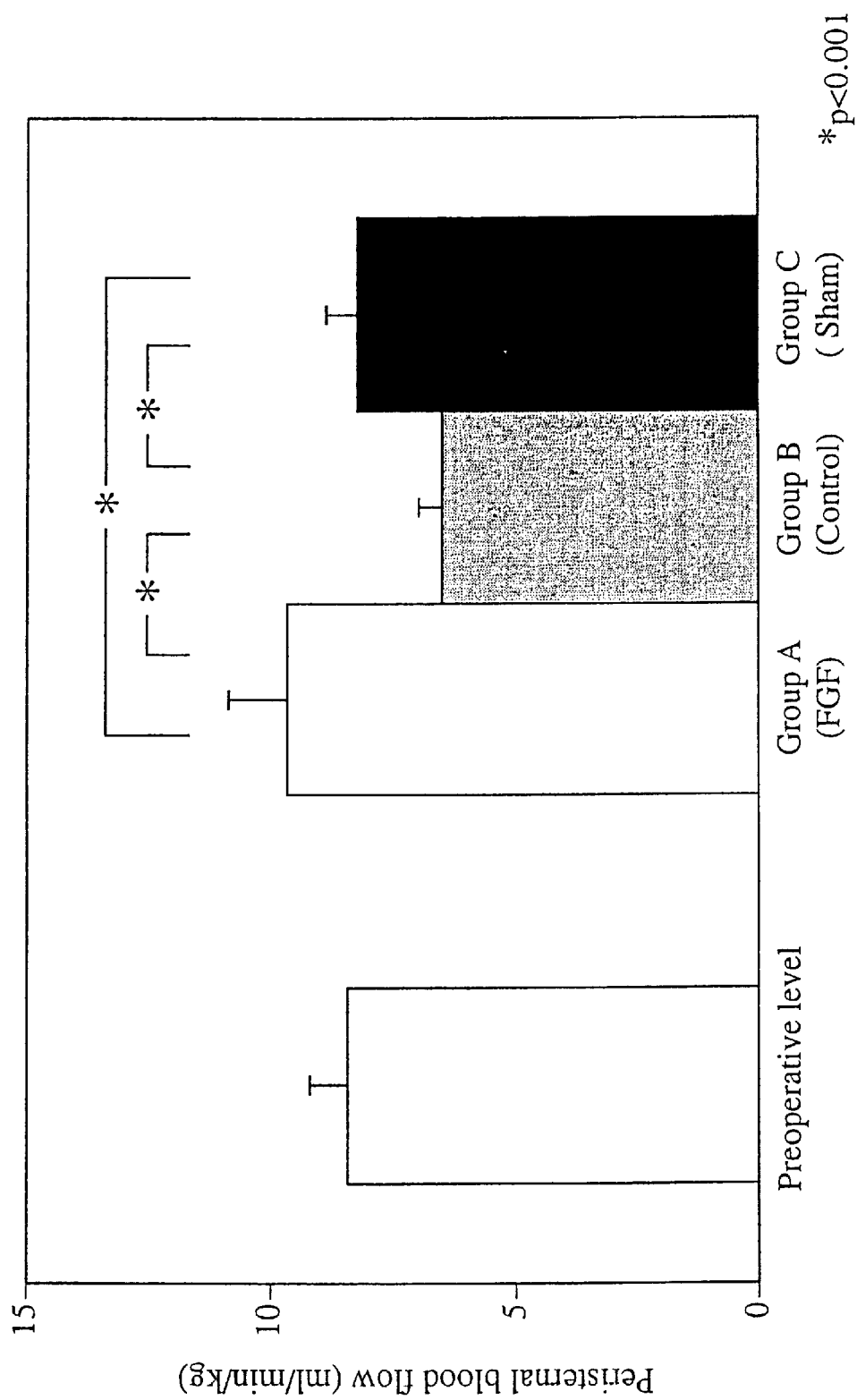
FIG. 1 is a graph showing the peristernal blood flow compared with preoperative level among three groups.

Hereinafter, the present invention is described in detail.

In the methods of present invention to enhance sternal healing after the sternotomy including the sternotomy with BITA removal, an agent(s) to enhance sternal healing to be applied to or around the sternum contains bFGF or some other angiogenetic factor(s) such as basic fibroblast growth factor (hereinafter sometimes referred to as "bFGF"), acidic fibroblast growth factor (hereinafter sometimes referred to as "aFGF"), vascular endothelial growth factor (hereinafter sometimes referred to as "VEGF"), tissue growth factor-β (hereinafter sometimes referred to as "TGF β"), hepatocyto growth factor (hereinafter sometimes referred to as "HGF"), bone morphogenetic protein (hereinafter sometimes referred to as "BMP"), platelet derived growth factor (hereinafter sometimes referred to as "PDGF"), tissue growth factor-α (hereinafter sometimes referred to as "TGF α"), other cytokines; and a protein, nucleic acid and gene which induce angiogenesis and/or osteogenesis can be used. Among the angiogenetic factors, bFGF may be most effective from the viewpoint of the sternal healing, in part because bFGF has both angiogenetic (i.e., create new vessels and increase blood supply to the sternum) and osteogenetic (i.e., help create bone tissue for the sternum) effects. However, other angiogenetic factors such as VEGF etc. may be useful under some condition such as mild sternal ischemia, etc.

The angiogenetic/osteogenetic factor(s) or their analogues can be used in the form of a solution comprising the angiogenetic/osteogenetic factor(s) such as bFGF, physiological or normal saline or other conventional anxiliary agents (glucose, sucrose, buffer, etc.), an injection or a spray using the solution, an ointment which contains the above solution, or a gel including hydrogel. Among these, the agent of the present invention is particularly preferable in the form of hydrogel since the gel stay on the target area for weeks and keep supplying the angiogenetic/osteogenetic factors until the sternum heals. The shape of the hydrogel can be either of a sheet, paste, granules, tubular, disk or microspheres. The agent of the present invention may take a route of topical or general application, but topical application is preferred because of less influence on other part of patients' body, less chance of complications and more effects on the target area (i.e., sternum).

When at least one of the angiogenetic/osteogenetic factors is used in the form of a hydrogel, the angiogenetic/osteogenetic factors are physically immobilized into the hydrogel by an intermolecular force, and accompanying with biodegradation of the hydrogen in vivo, the angiogenetic/osteogenetic factors are gradually released. As the physical immobilization, there may be mentioned, for example, an ionic bond, a coordination bond, a hydrophobic interaction, and the like. Sustained release of the angiogenetic/osteogenetic factors is controlled only by the biodegradation rate of the hydrogel, and not by the sustained release due to simple diffusion of the angiogenetic/osteogenetic factors. The biodegradation rate of the hydrogel is controlled by a water content of the hydrogel. When the water content is high, biodegradation rate of the hydrogel becomes high and when it is low, biodegradation rate of the same is low so that the sustained release period becomes a long term.

When the agent of the present invention is used, for example, in the form of a hydrogel, it can be prepared by incorporating bFGF as an active ingredient into a sustained release crosslinked gelatin gel. The gelatin gel as a raw material for the crosslinked gelatin gel used in the present invention is not specifically limited, and can be selected from generally available ones. Examples of the gelatin may include, for example, alkali-treated gelatin having an isoelectric point of about 4.9 (available from Nitta Gelatin Inc., Japan) and acid-treated gelatin having an isoelectric point of about 9.0 (available from Nitta Gelatin Inc., Japan). As a gelatin, not only one kind of gelatin may be used, but a mixture of gelatins different in physical properties such as solubility, molecular weight, isoelectric point and material may be used depending on the purposes to be used. As such a gelatin, those described, for example, in EP-A-0 702 959 may be used. As the other material for preparing the hydrogel of the present invention, there may be used, for example, collagen; hyaluronic acid, alginic acid, starch, pectin, chitin, chitosan or a derivative of these polysaccharides.

The crosslinking agent for crosslinking the gelatin, used in the present invention, can be selected from a material which is free from toxicity to a living body. Such a crosslinking agent may be mentioned, for example, glutaraldehyde, water-soluble carbodiimides such as 1-ethyl-3-(3-dimethylaminopropyl)carbodiimide hydrochloride and 1-cyclohexyl-3-(2-morpholinoethyl)carbodiimide-metho-p-toluenesulfonate, bis-epoxy compounds and formalin. Among these, glutaraldehyde and 1-ethyl-3-(3-dimethylaminopropyl)carbodiimide hydrochloride are particularly preferred.

The gelatin can be crosslinked by thermal treatment or irradiation with ultraviolet rays to obtain hydrogels with different biodegradabilities. A content of water in the gelatin hydrogel sheet is preferably 85% to 99% by weight, more preferably 90 to 98% by weight, particularly preferably 92 to 97% by weight based on the total weight of the gelatin hydrogel sheet.

Among the angiogenetic/osteogenetic factors, bFGF to be used as the effective ingredient of the agent to enhance sternal healing after the sternotomy especially after BITA harvesting is a well known angiogenetic or osteogenetic or growth factor as described. For example, in EP-A-0 493 737 and its presence is confirmed in human, bovine, mouse, rat, etc. Basically, bFGF from any animal origin has the same activity in vivo. However, among the agents used in the present invention to enhance sternal healing after sternotomy, it is preferred to use bFGF which has the same amino acid sequence as that of bFGF produced in human body (human bFGF) in view of antigenecity/osteogenecity. In addition to bFGF and above mentioned angiogenetic/osteogenetic factors, the analogue of bFGF as disclosed in EP-A-0 493 737 may also be used.

The agent of the present invention can be administered to on the surface of the sternum; inside of the sternum either alone, as a part of bone wax or glue, or on the surface of bar or nail or hinge type of device; in direct contact with the fracture site of the rib or cartilage (i.e., soft bone) or their junction; or on the bed of the internal thoracic artery(ies).

In the present invention, a few methods of enhancing sternal healing after sternotomy can be specifically mentioned.

The first method is to spray or oint at least one of the angiogenetic/osteogenetic factors such as bFGF, aFGF, TGF β, VEGF, HGF, BMP, PDGF, TGF α, other cytokines or gene which makes above material(s) to the sternal edge (and ITA bed(s) in patients who had ITA(s) harvested for coronary bypass surgery).

The second method is to inject a solution containing at least one of the angiogenetic/osteogenetic factors such as bFGF, aFGF, TGF β, VEGF, HGF, BMP, PDGF, TGF α, other cytokines or gene which makes above material(s) to the sternal edge or tissue around (and ITA bed(s) in patients who had ITA(s) harvested for coronary bypass surgery).

The third method is to use a biodegradable hydrogel which we developed; the hydrogel comprises acidic gelatin to enable at least one of the angiogenetic/osteogenetic factors such as bFGF, aFGF, TGF β, VEGF, HGF, BMP, PDGF, TGF α, other cytokines or gene which makes above material(s) to be released at the site of action for extended time period. The hydrogel can be applied to the posterior (i.e., inner) surface of the sternum, but anterior (i.e., outer) surface as well; the hydrogel can be applied to the ITA bed(s) to restore the blood supply of the sternum from chest wall.

The fourth method is to insert a material which contains at least one of the angiogenetic/osteogenetic factors such as bFGF, aFGF, TGF β or VEGF, HGF, BMP, PDGF, TGF α, other cytokines or gene of the above material(s) to the bone marrow (i.e., inside) of the sternum. This fourth method can be applied together with the above method(s) to further enhance sternal healing (i.e., from both inside and outside).

An effective dose of the agent to enhance sternal healing after sternotomy in accordance with the present invention varies depending on the degree of diseases, age or condition of the patient, etc. But the dose is generally in the range of about 0.1 μg to 10 mg/sternotomy site, as the effective ingredient in the case of fracture. In order to accelerate healing, generally preferred routes for application is to administer the agent in direct contact with the sternotomy site: (1) from outside (i.e., on the surface of the sternal), (2) from inside (i.e., in the sternum or sternal bone marrow), and (3) on the ITA bed (i.e., the area where ITA and its pedicle used to sit).

The above-mentioned agent of the present invention is also effective for regenerating bone at sternum after sternotomy or subjecting to vascularization around sternum after sternotomy. Thus, for regenerating bone at sternum after sternotomy or for subjecting to vascularization around sternum after sternotomy, the similar method as mentioned above can be applied to the patients.

EXAMPLES

Hereinafter the present invention is described with reference to the examples.

Example 1

An effect of present invention is evaluated in the enhanced sternal healing by topical use of bFGF after sternotomy and removal of BITA in rats.

Gelatin with an isoelectric point of 4.9 was isolated from bovine bone collagen with $Ca(OH)_2$ (Nitta Gelatin Co., Osaka, Japan) by alkaline process. The weight-average molecular weight of the gelatin was 99000 when measured by gel filtration chromatography relative to standard polyethylene glycol samples. Human recombinant bFGF with an isoelectric point of 9.6 was supplied from Kaken Pharmaceutical Co., Tokyo, Japan.

(i) Preparation of BFGF-incorporating Gelatin Hydrogel Sheets

Gelatin in 10 wt % aqueous solution was chemically crosslinked with various amounts of glutaraldehyde at 25° C. to prepare sheets with different extents of crosslinking. Briefly, 4.5 ml of an aqueous gelatin solution containing glutaraldehyde was cast into a Teflon mold (5×5 cm², 1.8 mm depth). Following the crosslinking reaction, which lasted for 12 hours at 25° C., the resulting hydrogel sheets were immersed in 50 mM of glycine aqueous solution at 37° C. for one hour to block residual aldehyde groups of glutaraldehyde, rinsed by double-distilled water, 100% ethanol, and autoclaved double-distilled water to obtain the sterilized sheets. These were freeze dried, followed by impregnation with an aqueous solution containing 100 μg of bFGF, to obtain gelatin hydrogels that incorporated bFGF. The thus prepared hydrogel sheets were rectangle shaped (1×10 mm) and 0.7 mm thick. All experimental processes were done under sterile conditions.

(ii) Animal Experiment

Fifteen male Wistar rats weighing between 300 g and 400 g were orally intubated after anesthetized with ether, and were ventilated on a volume-cycled small animal ventilator (Rodant ventilator Model 683, HARVARD, USA). Anesthesia were maintained during the operation with 1% to 2% isoflurane. After midline skin incision at supine position, bilateral major pectoris muscles were divided from the junction of the sternum and bilateral intercostal muscles were exposed. Median sternotomy was performed with microstriker carefully. The bleeding from the bone marrow was stopped with the use of bone wax (NESTOR, Nippon Shoji, Japan). BITA were ligated with 6-0 polypropylene sutures at the beginning and distal bifurcation of ITA, besides BITA were destroyed by electrical coagulator. Gelatin hydrogel sheets incorporated bFGF (100 μg/sheet) were placed and fixed with 6-0 polypropylene sutures instead of the defect of BITA. As controls, we performed median sternotomy alone and just the BITA removal on the same way. After a positive endoexpiratory pressure was applied to fully inflate the lung, the sternum was closed by 4 peristernal interrupted sutures with 4-0 Nespolenesutures. The muscle layer and skin were carefully sutured with 4-0 nylon monofilaments. Streptomycin was administered intramuscularly just after skin closure (50 mg/rat).

The fifteen rats were divided into three groups: Group A had the removal of the BITA and gelatin hydrogel sheets incorporated bFGF on the sternum after a median sternotomy, Group B had just the removal of the BITA, Group C had intact BITA (5 animals each). Five animals, which were died with 2 postoperative intrapericardial bleeding, 2 respiratory failure or 1 infection were excluded from the study. The rats were sacrificed by intravenous administration of sodium pentobarbital at an over-dose 4 weeks after surgery. The sternum was taken out and fixed in 10 wt % formaldehyde solution in PBS for 4 days to assess the bone regeneration.

(iii) Measurement of Peristernal Blood Flow

The peristernal blood flow was measured using a non-contact laser flowmeter (ALF21N, Advance, Tokyo, Japan) before a median sternotomy, after closure of the sternum and 2 or 4 weeks after surgery. This device instantaneously measures capillary blood perfusion parameters (blood flow, volume and velocity). Only blood flow was monitored and recorded (mL/min/100 g) in this study. A beam of laser light was directed through an optic fiber to a measuring probe with a diameter of 3.0 mm. The probe was placed over intercostal muscle near the sternum detachedly 10 mm in a straight line so that measurement area to be investigated was about 5 mm in diameter and 1 mm in depth. The He-Ne light was then switched to the diode laser (2 mW, 780 nm) to measure blood flow around the sternum, which was calculated using the Doppler shift. The probe included two optic fibers: one for laser illumination and the other for receiving reflected and dispersed light. Three readings for each measurement were recorded after stable baselines were obtained and averaged.

(iv) Histological Assessment of Angiogenesis

Arterioles were counted in preparations stained with hematoxylin-eosin and azan. Five fields (5 mm by 5 mm) were randomly chosen from the peristernal area at the inside of the sternum. We assessed the density of arterioles in each 5 mm by 5 mm field by counting the mean number of vessels in five randomly chosen unit areas (500 μm by 500 μm) using a section ocular micrometer (Olympus, Tokyo, Japan) at ×400 magnification. Total number of vessels in 25 unit areas (5 fields with 5unit areas in each field) were counted.

(v) Assessment of Bone Formation

Bone regeneration around the sternum was assessed by Dual Energy X-ray Absorptometry (DEXA) and histological examinations. The bone mineral density (BMD) around the sternum was measured by DEXA utilizing a bone mineral analyzer (Dichroma Scan 600, Aloka Co., Tokyo, Japan) at 4 weeks after a median sternotomy into three groups. The instrument was calibrated with a phantom of known mineral content. Each scan was performed at a speed of 20 mms$^{-1}$ and the scanning length was 1 mm. DEXA measurement was performed the limits of the sternum from third to sixth rib per each experimental group.

Bone specimens were demineralized in 10 wt % EDTA solution at 4° C. for 3 days, embedded in paraffin and section at 10 μm in thickness. The sections were prepared to cut as being divided into 4 equal parts of the sternum and stained with hematoxylin-eosin (HE) at 2 and 4 weeks after surgery. The histological sections were analyzed using a microscope with a video camera connected to an image analysis system (SP-1000, Olympus, Tokyo, Japan). Areas of new bone of the sternum per each sections were measured at 2× magnification.

(vi) Statistical Analysis

All the data were analyzed by one-way ANOVA to assess statistical significance among experimental groups. Experimental results were expressed as mean ± standard error. The test of significance was performed at the 95% confidence interval compared to the control group.

(vii) Peristernal Blood Flow

Results are summarized in FIG. 1. FIG. 1 is a peristernal blood flow before and after the surgery in each group. In Group A (both bFGF and hydrogel was applied), peristernal blood flow was larger than in Group B (Control, no bFGF and no hydrogel was used) Group C (Sham, no bFGF but hydrogel was used). This suggests that bFGF-containing hydrogel applied on the posterior (i.e., inner) surface of the sternum and internal thoracic artery beds helped angiogenesis on/around the sternum. Preoperative peristernal blood flow (PBF) was 8.6±0.6 (mean ±SD) ml/min/100 g. Though PBF after a median sternotomy alone had no significant changes, it was significantly reduced to 8.5+0.6 ml/min/100 g after the BITA removal. PBF at 4 weeks after surgery in Group A, Group B or Group C were 9.7±1.2, 6.5±0.6, or 8.2±0.5 ml/min/100 g, respectively. Significant differences were noted in the three groups ($p<0.001$).

(viii) Histological Assessment of Angiogenesis

Figure 2A:
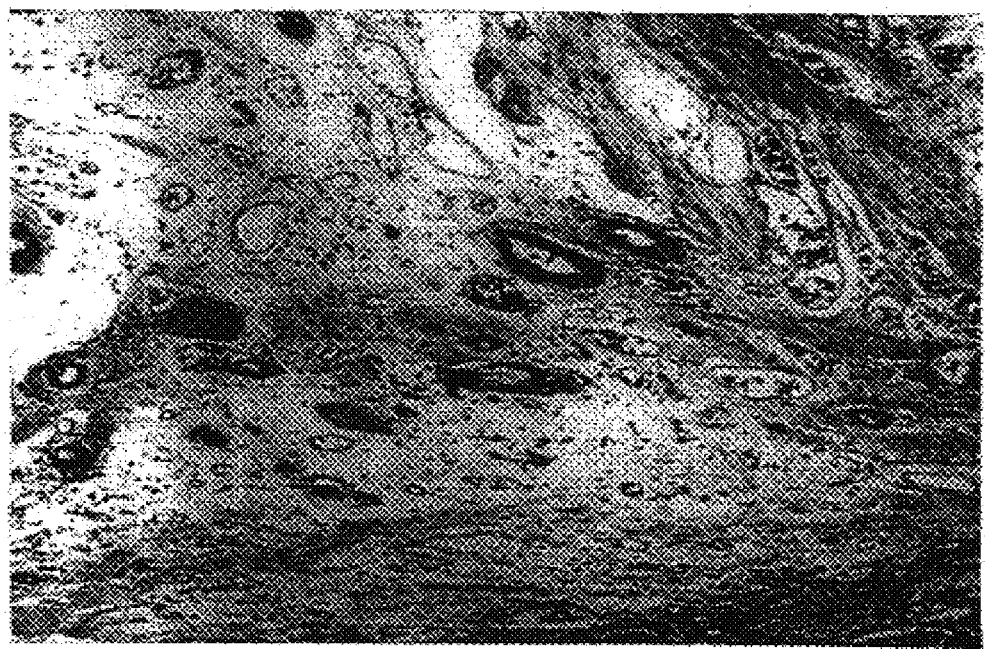
Figure 2B:
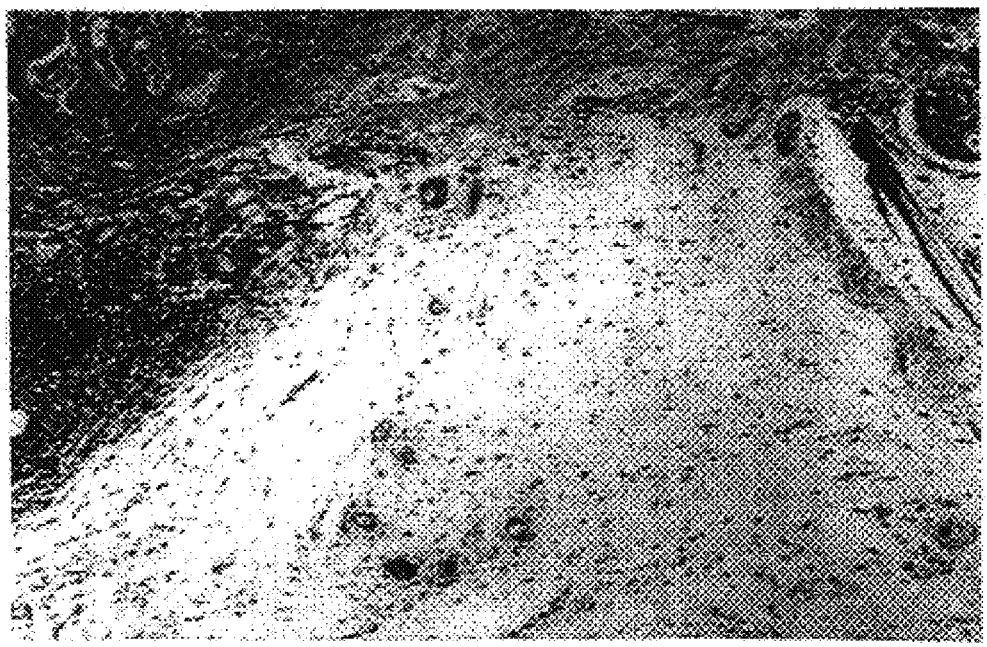
Figure 2C:
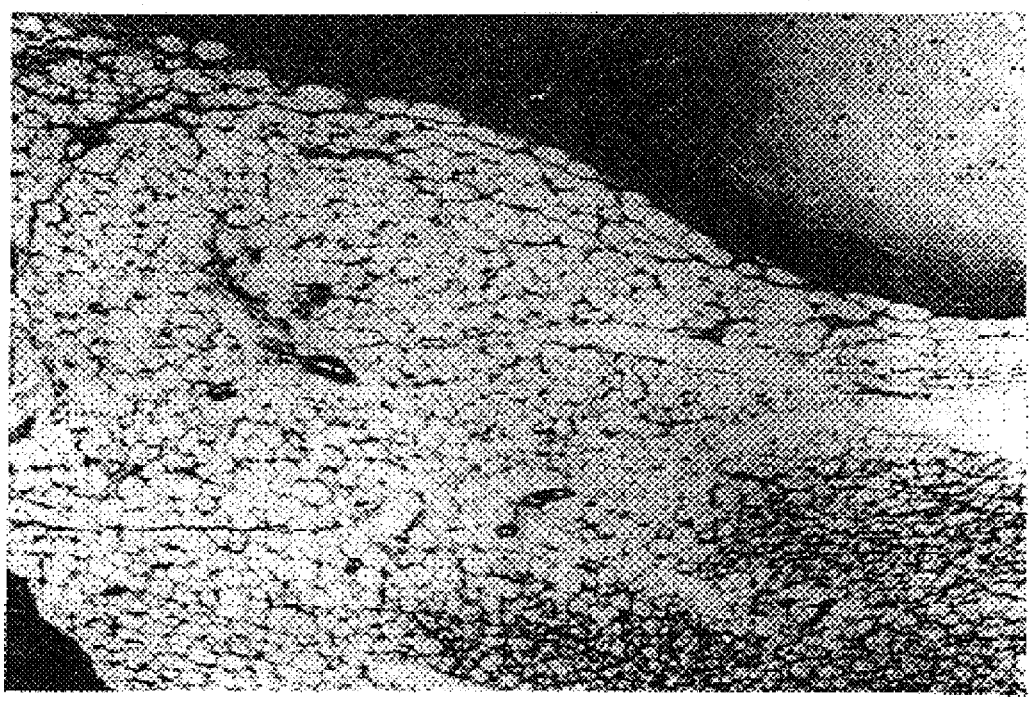

Histological study of the anogiogenesis around the sternum confirmed this increase in vascular number. There were more capillaries and arteioles (10 to 50 $\mu$m in diameter) around the sternum in Group A than in Group B and C (FIGS. 2A to 2C). FIGS. 2A, 2B, and 2C show photomicrographs of the connective tissue around the sternum four weeks after the surgery. In Group A (both bFGF and hydrogel was applied) a lot of angiogenesis is seen (FIG. 2A) while in Group B (Control, no bFGF and no hydrogel was used, FIG. 2B) and Group C (Sham, no bFGF but hydrogel was used, FIG. 2C) only little angiogenesis is observed. The results strongly suggest that the increased blood peristernal flow of Group A seen in FIG. 1 is caused by the angiogenesis. FIG. 3 shows the number of arterioles and capillaries/unit area around the sternum among three groups. That is, FIG. 3 shows a vascular number around the sternum in each group. In Group A (both bFGF and hydrogel was applied) larger number of the vessels were seen in the connective tissue around the sternum. On the other hand, In Group B (Control, no bFGF and no hydrogel was used) and in Group C (Sham, no bFGF but hydrogel was used), significantly less vascular number was seen. The number of arterioles and capillaries/unit area around the sternum was increased more markedly in Group A than in other two groups (Group A: 30.5±3.2, Group B: 15.8±2.7, Group C: 12.3±1.5 vessels/unit area, $P<0.01$).

(ix) Assessments of Bone Formation

FIGS. 4A and 4B show results of the BMC (bone mineral content) and BMD (bone mineral density) measurements of the sternum of rats 4 weeks after various surgeries, respectively. That is, FIG. 4 shows a bone mineral content (FIG. 4A) and bone mineral density (FIG. 4B) in each group. In Group A (both bFGF and hydrogel was applied) bone mineral content was more than Group B (Control, no bFGF and no hydrogel was used) and Group C (Sham, no bFGF but hydrogel was applied); this suggests Group A had more regeneration (i.e., healing) of the sternum. In all the groups bone mineral density was at the same level; this suggests that Group A had regenerated sternum with normal quality.

The BMC in Group A which was 65.5±15.7 mg was significantly larger than in Group B and C (Group B: 47.6±6.4, Group C: 41.3±17.5 mg). On the other hand, the BMD did not had significantly changes among three groups (Group A: 51.1±8.1, Group B: 50.0±6.1, Group C: 43.7±8.5 mg/mm$^2$).

Figure 5:
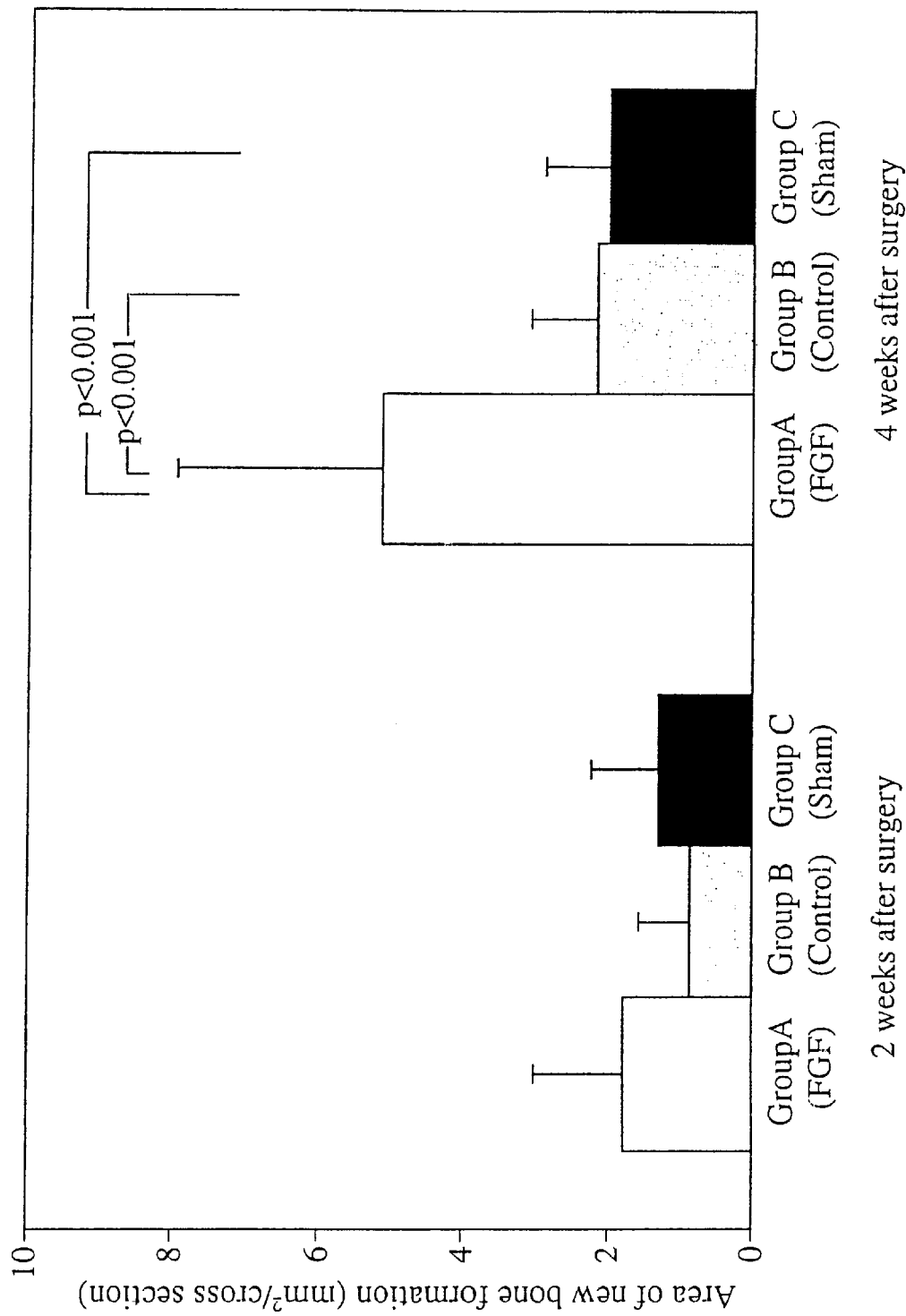
FIG. 5 is a graph showing comparison of area of new bone formation among three groups two or four weeks after surgery.

FIG. 5 demonstrates results of the area of new bone formation of the sternum among all groups 2 and 4 weeks after various surgeries. FIG. 5 shows an area of new bone formation 2 weeks and 4 weeks after the surgery. Two weeks after the surgery, Group A (both bFGF and hydrogel was applied) tended to have more bone formation than Group B (Control, no bFGF and no hydrogel was used) and Group C (Sham, no bFGF but hydrogel was used), and this difference became much larger and significant two weeks later (i.e., four weeks after the surgery). Two weeks after surgery, the area of new bone formation in Group A had a tendency to be larger than in Group B and C, but there are no significant differences among three groups (Group A: 1.79±1.22, Group B: 0.87±0.70, Group C: 1.37±0.92 mm$^2$). On the other hand, Group A had significantly larger area of new bone formation four weeks after surgery than other two groups (Group A: 5.13±2.82, Group B: 2.17±0.91, Group C: 2.01±0.89 mm$^2$).

Figure 6A:
FIGS. 6A to 6C are photomicrographs showing histological cross sections obtained from the sternum two weeks after surgery wherein Group A is bFGF, Group B is control and Group C is sham.
Figure 6B:
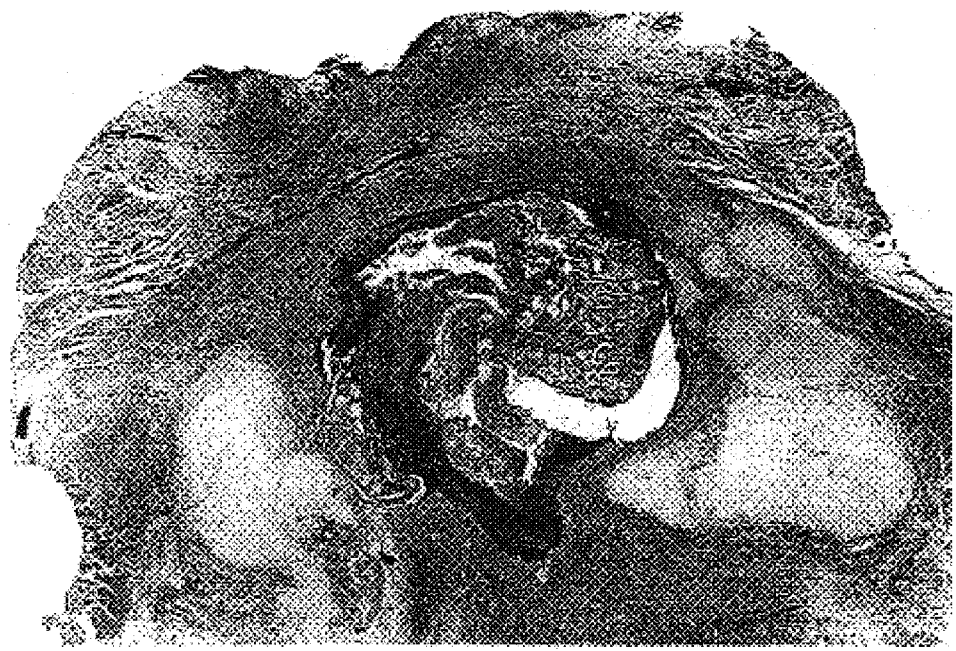
Figure 6C:
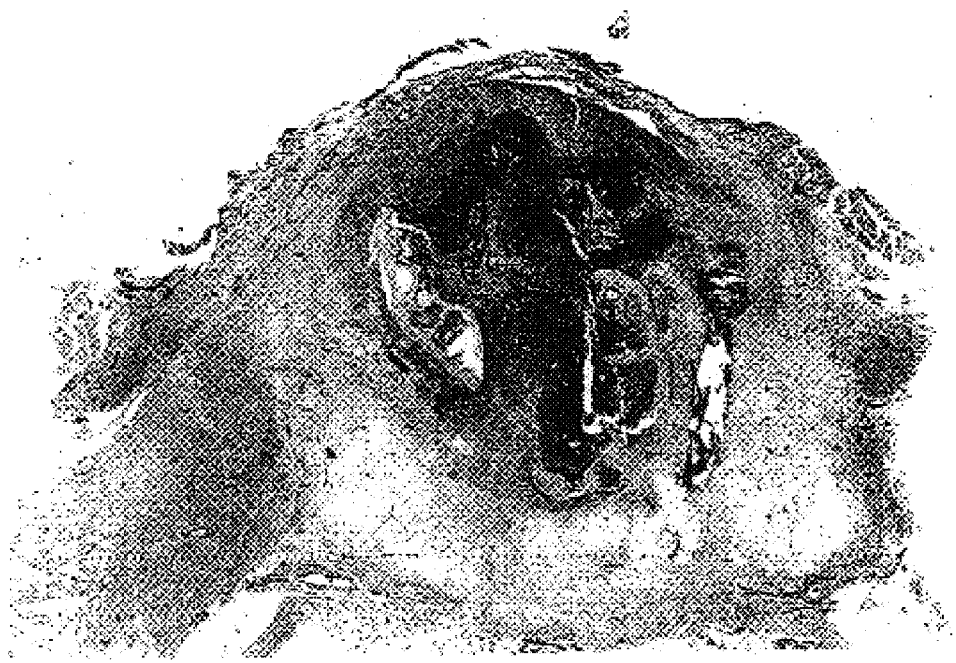
Figure 7A:
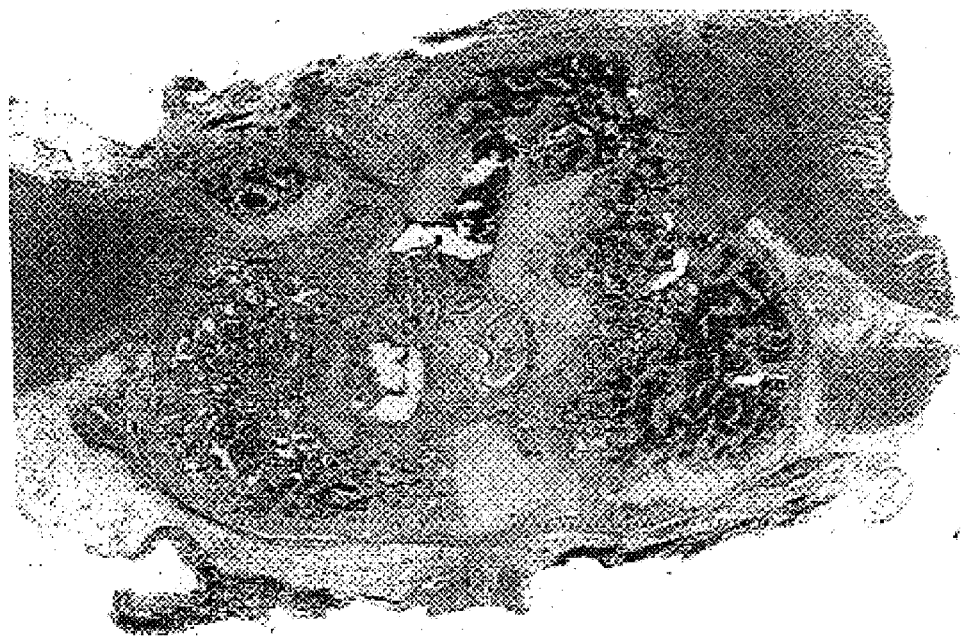
FIGS. 7A to 7C are photomicrographs showing histological cross sections obtained from the sternum four weeks after surgery wherein Group A is bFGF, Group B is control and Group C is sham.
Figure 7B:
Figure 7C:
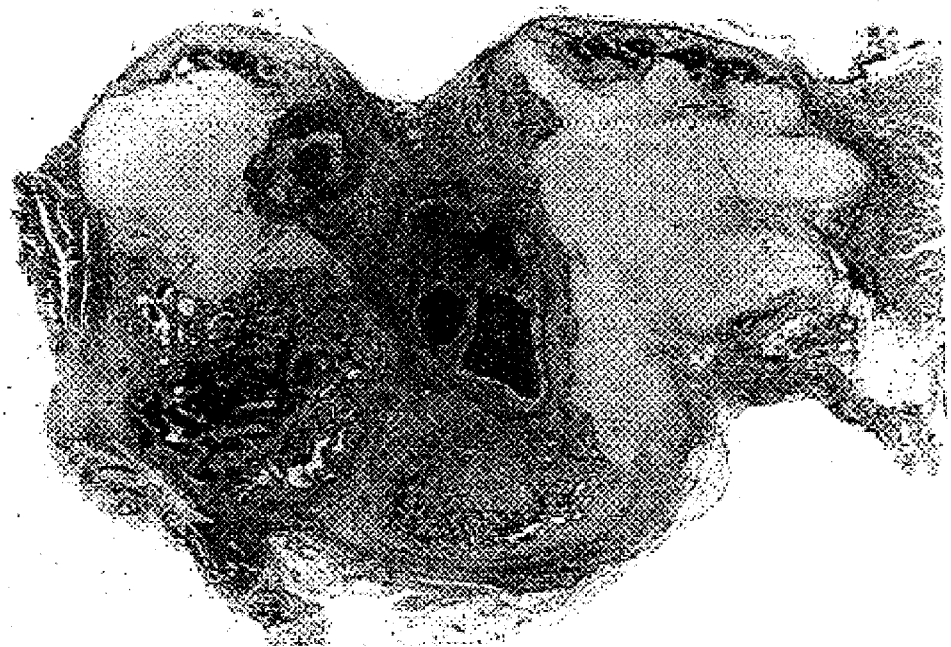

FIGS. 6A–6C and 7A–7C show histological sections of the sternum 2 and 4 weeks after different surgery, respectively. That is, FIGS. 6A, 6B, and 6C are photomicrographs of the cross sections from the sternum two weeks after the surgery. In Group A (both bFGF and hydrogel was applied, FIG. 6A) and Group C (Sham, no bFGF but hydrogel was used, FIG. 6C), the sternum already started healing. On the other hand, in Group B (Control, no bFGF and no hydrogel were used, FIG. 6B) sternum did not start healing. Also, FIGS. 7A, 7B, and 7C are photomicrographs of the cross sections from the sternum four weeks after the surgery. In Group A (both bFGF and hydrogel was applied), the sternum healed almost completely and there was no mal- or hyper-healing of the sternum (FIG. 7A). On the other hand, in Group B (Control, no bFGF and no hydrogel were used, FIG. 7B) and in Group C (Sham, no bFGF but hydrogel was used, FIG. 7C) sternum did not heal well. Two weeks after surgery, some enchondral ossification around the original sternum was observed in Group A and C, but was not observed in Group B. Four weeks after surgery Group B and C had partial enchondral ossification around the original sternum. On the contrary, Group A had nearly completely healed sternum filled with a regenerated bone tissue.

In the present invention, a few methods to enhance sternal healing after sternotomy including sternotomy after BITA removal can be provided. According to the data obtained in the experiment, enhanced sternal healing was caused by angiogenesis of the sternum and the tissue around and by osteogenesis; both the angiogenesis and the osteogenesis was induced by the angiogenetic/osteogenetic factor (e.g., bFGF in this experiment) applied topically.

Example 2

An effect of present invention is evaluated in the enhanced sternal healing by topical use of bFGF after sternotomy and removal of BITA in beagle dogs.

(i) Preparation of BFGF-Incorporating Gelatin Hydrogel Sheets

In the same manner as in (i) of Example 1, an alkali-treated gelatin having an isoelectric point of 4.9 was chemically crosslinked with glutaraldehyde at 25° C. to prepare sterilized sheets. These were freeze dried, followed by impregnation with an aqueous solution containing 100 $\mu$g of bFGF, to obtain gelatin hydrogels that incorporated bFGF. The thus prepared hydrogel sheets were rectangle shaped (1×10 mm) and 0.7 mm thick. A water content of the respective hydrogel sheets was 95%. All experimental processes were done under sterile conditions.

(ii) Animal Experiment

Eight beagle dogs weighing between 10 kg to 12 kg were orally intubated after anesthetized with ether and subjected to median sternotomy at supine position, and bilateral internal thoracic artery of each dog was peeled off from the starting position to the height of xiphoiditis by using an electric scalpel with a pedicled fashion. The peeled bilateral internal thoracic artery was completely separated and cut by using a 1-0 silk thread at the central side and the peripheral side, and removed.

These eight dogs were divided into two groups: Group A had the removal of the BITA and bFGF (100 μg/sheet) -incorporated gelatin hydrogel sheet was adhered on the sternum after a median sternotomy, and Group B had just the removal of the BITA (4 animals each). The gelatin hydrogel sheet was prepared by chemically cross-linking an alkali-treated gelatin having an isoelectric point of 4.9 with glutaraldehyde. The gelatin hydrogel sheet contained water in an amount of 95% by weight based on the total gelatin hydrogel sheet.

(iii) Assessment of Bone Formation

Bone regeneration around the sternum after 4 weeks was assessed by Bone Scintigram (using Technetium 99 methylene diphosphonate; hereinafter abbreviated to as "Tc-99-MDP"), X-ray photography of the sternum and Dual Energy X-ray Absorptometry (DEXA).

(iv) Bone Scintigram Analysis

Figure 8A:
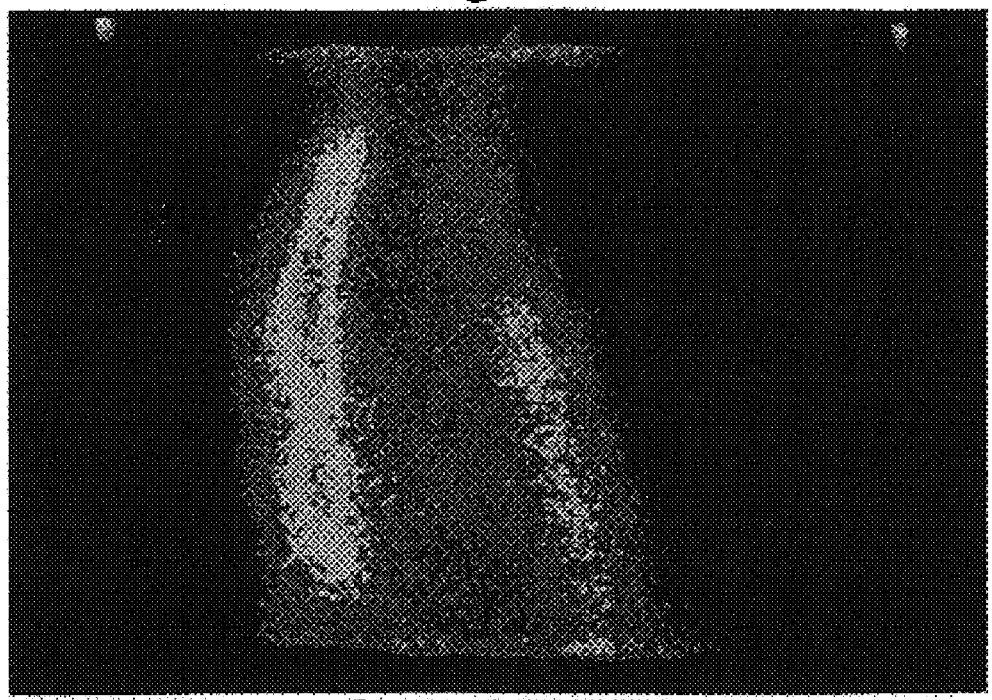
FIGS. 8A and 8B are photographs showing bone scintigram obtained from the sternum four weeks after surgery wherein Group A is bFGF and Group B is control.
Figure 8B:
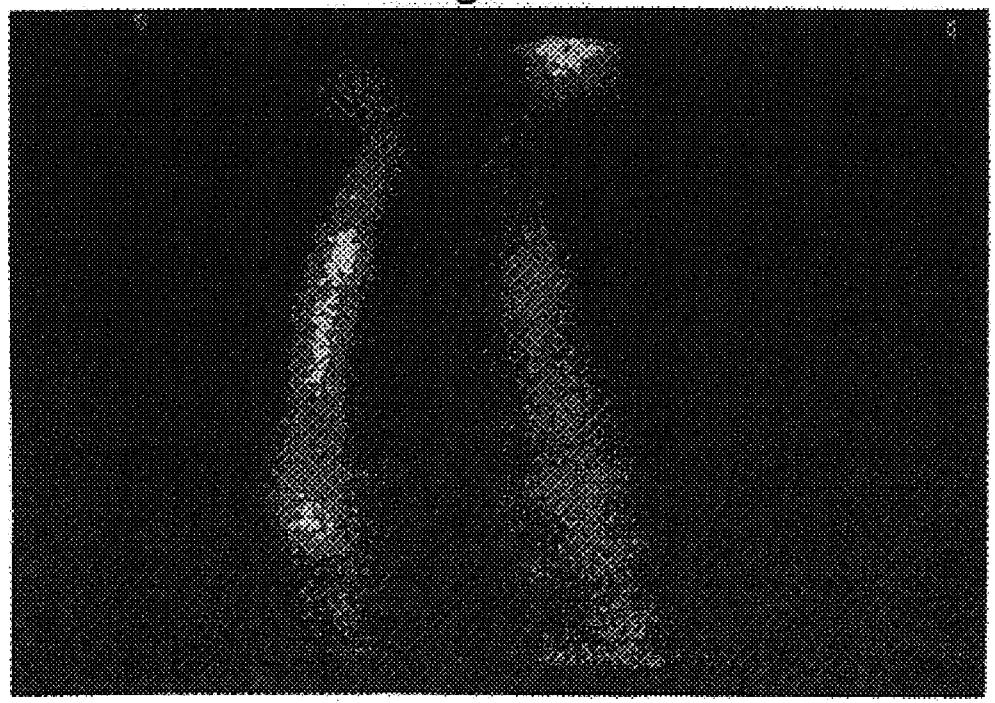

Tc-99-MDP was intravenously administered to the respective dogs after 4 weeks from the surgery and bone scintigrams of the dogs were photographed after 60 minutes from the administration. The results are shown in FIGS. 8A (Group A) and 8B (Group B). As can be seen from these photographs, it can be clearly admitted that Tc-99-MDP was more accumulated at the sternum in Group A than that of Group B.

Also, the sternum was divided into three groups as regions of interests (ROI), and ratios of shadows at the respective regions were calculated based on that of the anterior mediastinale portion as the reference region (ref-ROI) to effect quantitative evaluation. As a result, as shown in FIG. 9, after 30 minutes of the Tc-99-MDP administration, Group A was 234.9±31.0% and Group B was 176.2±39.0%, and after 60 minutes of the Tc-99-MDP administration, Group A was 282.7±22.9% and Group B was 174.2±27.2%. Thus, significant differences were noted in these groups ($p<0.001$).

(v) X-ray Photography of Sternum

Figure 10A:
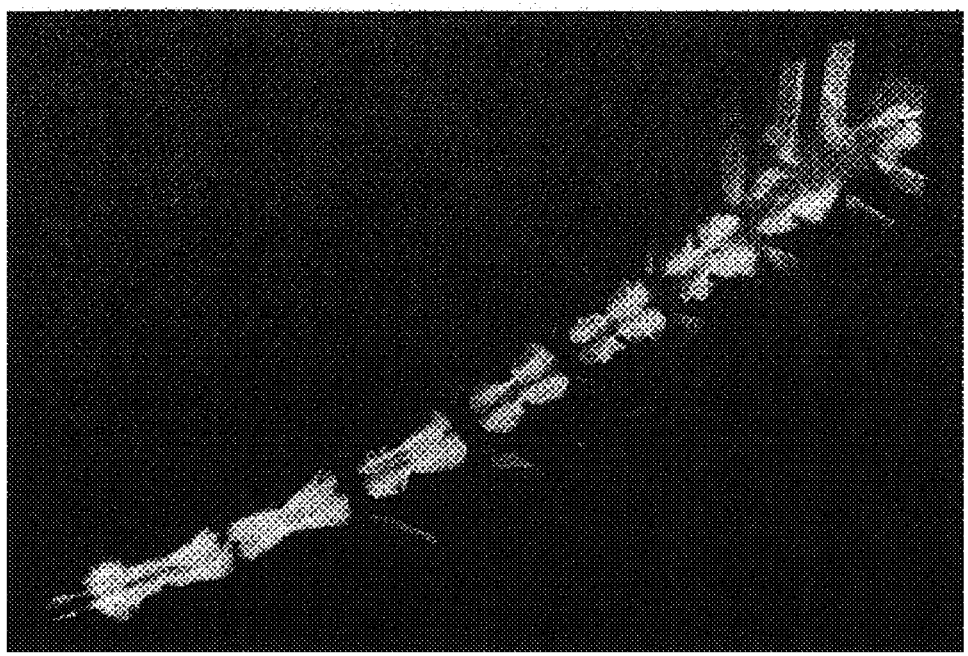
FIGS. 10A and 10B are X-ray photographs showing the sternum four weeks after surgery wherein Group A is bFGF and Group B is control.
Figure 10B:
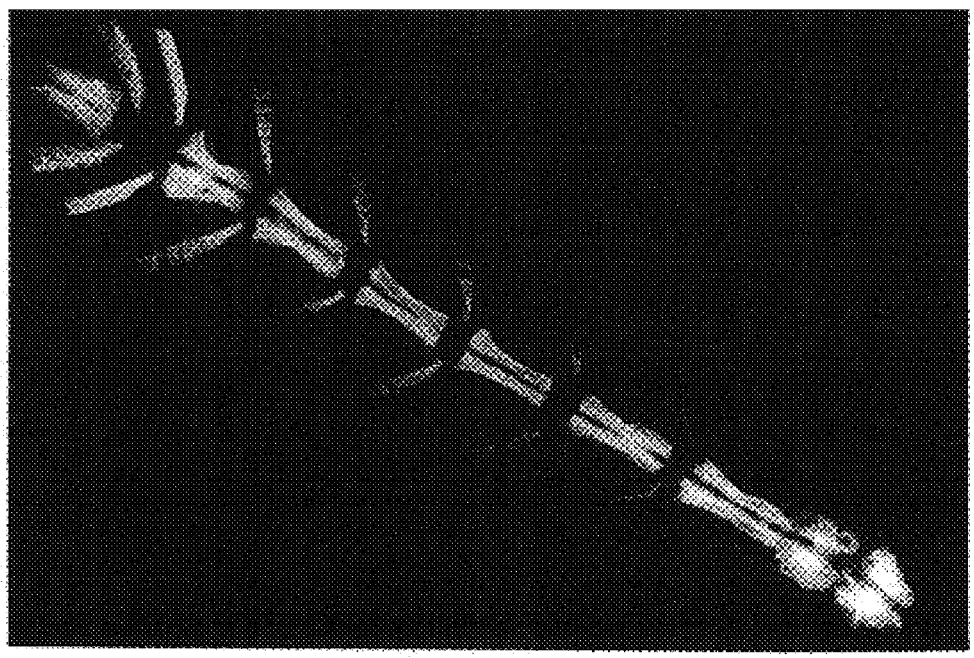

Bone regeneration around the sternum after 4 weeks from the surgery was assessed by X-ray photography. The results are shown in FIGS. 10A (Group A) and 10B (Group B).

In Group A, sufficient bone regeneration can be admitted at all the portions, while in Group B, there are many portions in which bone regeneration was insufficient and some portions were partially separated.

(vi) Dual Energy X-Ray Absorptometry (DEXA)

Figure 11A:
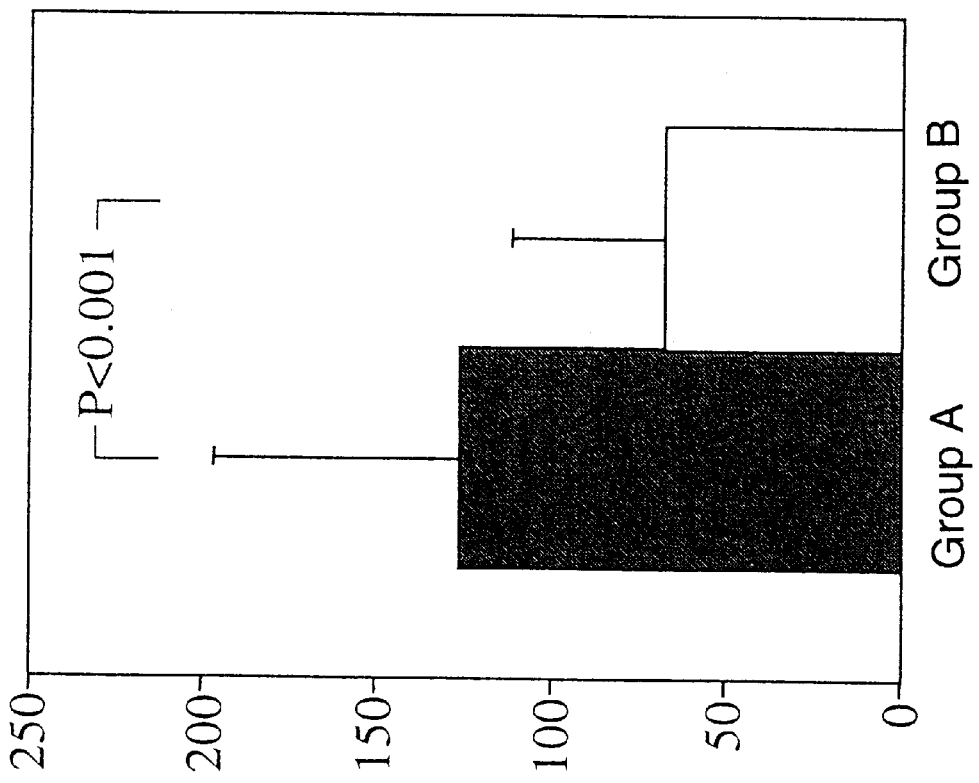
FIGS. 11A and 11B are graphs showing comparison of bone amount and bone density of the sternum four weeks after surgery, respectively, wherein Group A is bFGF and Group B is control.
Figure 11B:
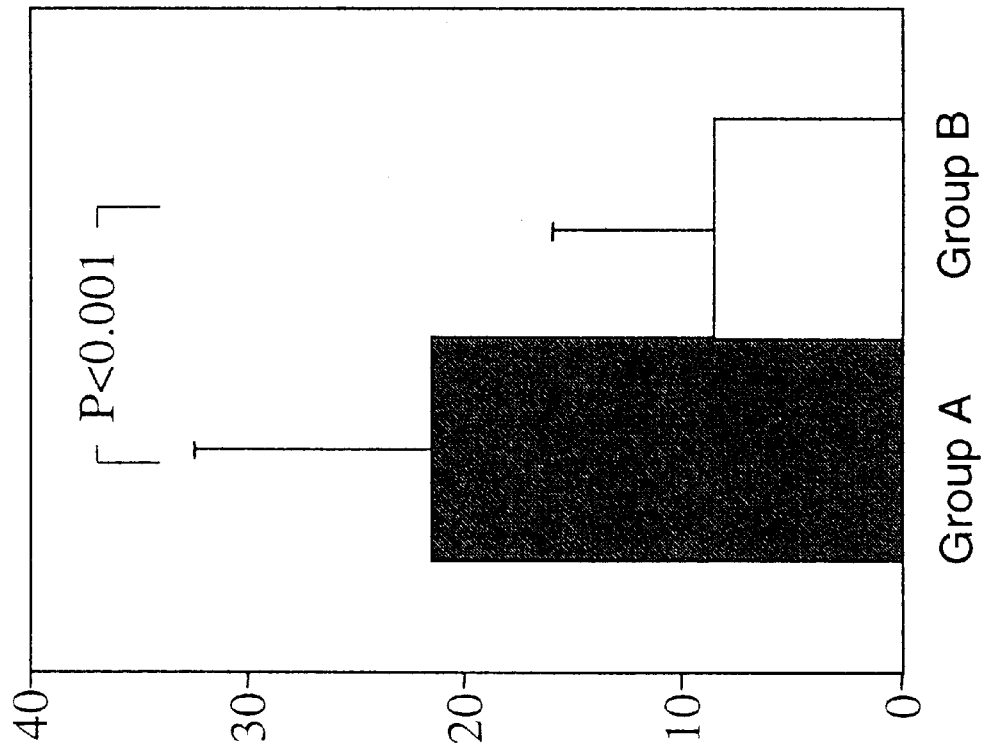

To evaluate sternum regeneration quantitatively, a region of interest (ROI) with a size of 0.1 cm×1.0 cm was set at the sternum incision portion, and a bone amount and a bone density at the portion was measured by using DEXA. The measured portions are the sternum incision portions between the first and the sixth costae in both of the sterna. The results are shown in FIG. 11. As can be seen from FIG. 11, the bone amount of Group A was 21.4±11.1 mg while it was 8.6±7.4 mg in Group B, and the bone density of Group A was 125.8±70.5 mg/mm$^2$ while it was 66.7±44.3 mg/mm$^2$ in Group B. Thus, it can be understood that Group A showed markedly higher values than those of Group B so that significant differences were noted in these groups ($p<0.001$).

What is claimed is:

1. A method to enhance sternal treatment after a sternotomy which consists of directly applying to an area at or around the sternum a pharmaceutical composition wherein the pharmaceutical composition is mixed with a hydrogel carrier and said pharmaceutical composition comprises (a) at least one agent, wherein said agent is selected from the group consisting of an angiogenetic factor, an osetogenetic factor and their analogues, and (b) a pharmaceutically acceptable carrier or diluent.

2. The method according to claim 1, wherein said hydrogel is a crosslinked hydrogel comprising an alkali-treated gelatin having an isoelectric point of about 4.9 or acid-treated gelatin having an isoelectric point of about 9.0, and a crosslinking agent.

3. The method according to claim 1, wherein the agent is selected from group consisting of basic fibroblast growth factor, acidic fibroblast growth factor, vascular endothelial growth factor, tissue growth factor-β, hepatocyte growth factor, bone morphogenetic protein, platelet derived growth factor, tissue growth factor-α, a cytokine, and a protein, nucleic acid or a gene which induces angiogenesis and/or osteogenesis.

4. The method according to claim 1, wherein the agent is basic fibroblast growth factor or an analogue thereof.

5. The method according to claim 1, wherein the composition is administered to the area in an amount of about 0.1 μg to 10 mg.

6. A method of regenerating bone at sternum after sternotomy which comprises directly applying to an area at or around the sternum a pharmaceutical composition wherein the pharmaceutical composition is mixed with a hydrogel carrier and said pharmaceutical composition comprises (a) at least one agent, wherein said agent is selected from the group consisting of an angiogenetic factor and an osteogenetic factor, and (b) a pharmaceutically acceptable carrier or diluent.

7. A method of subjecting to vascularization around sternum after sternotomy which comprises directly applying to an area at or around the sternum a pharmaceutical composition wherein the pharmaceutical composition is mixed with a hydrogel carrier and said pharmaceutical composition comprises (a) at least one agent, wherein said agent is selected from the group consisting of an angiogenetic factor and an osteogenetic factor, and (b) a pharmaceutically acceptable carrier or diluent.

8. A method of treating a fracture site after sternotomy which comprises applying in direct contact with the fracture site of a rib, cartilage or their junction a pharmaceutical composition wherein the pharmaceutical composition is mixed with a hydrogel carrier and said pharmaceutical composition comprises (a) at least one agent, wherein said agent is selected from the group consisting of an angiogenetic factor and an osteogenetic factor, and (b) a pharmaceutically acceptable carrier or diluent.

9. The method of claim 1, wherein the sternotomy is a stemotomy with removal of at least one internal thoracic artery.

10. The method of claim 6, wherein the sternotomy is a sternotomy with removal of at least one internal thoracic artery.

11. The method of claim 7, wherein the sternotomy is a sternotomy with removal of at least one internal thoracic artery.

12. The method of claim 8, wherein the sternotomy is a sternotomy with removal of at least one internal thoracic artery.

13. A method to enhance sternal treatment after a stemotomy which comprises directly applying to an area at or around the sternum a pharmaceutical composition, wherein only native sternum is present in the area where the pharmaceutical composition is applied, wherein the pharmaceutical composition is mixed with a hydrogel carrier and said pharmaceutical composition comprises (a) at least one agent, wherein said agent is selected from the group consisting of an angiogenetic factor, an osteogenetic factor and their analogues, and (b) a pharmaceutically acceptable carrier or diluent.

14. A method to enhance sternal healing after a sternotomy comprising directly applying to an area at or around the sternum a pharmaceutical composition with no osteoimplant present, wherein the pharmaceutical composition is mixed with a hydrogel carrier and said pharmaceutical compositions comprises (a) at least one agent, wherein said agent is elected from the group consisting of an angiogenetic factor, an osteogenetic factor, and (b) a pharmaceutically acceptable carrier or diluent.

* * * * *